(12) United States Patent
Leiber

(10) Patent No.: US 9,693,768 B2
(45) Date of Patent: Jul. 4, 2017

(54) MENISCUS REATTACHMENT DEVICE

(75) Inventor: Valentin Leiber, Tuttlingen (DE)

(73) Assignee: Glaser GmbH Surgical Instruments, Tuttlingen (DE)

( * ) Notice: Subject to any disclaimer, the term of this patent is extended or adjusted under 35 U.S.C. 154(b) by 418 days.

(21) Appl. No.: 13/977,925

(22) PCT Filed: Nov. 30, 2011

(86) PCT No.: PCT/EP2011/005994
§ 371 (c)(1),
(2), (4) Date: Oct. 3, 2013

(87) PCT Pub. No.: WO2012/072244
PCT Pub. Date: Jun. 7, 2012

(65) Prior Publication Data
US 2014/0018827 A1    Jan. 16, 2014

(30) Foreign Application Priority Data
Nov. 30, 2010   (DE) .................. 10 2010 060 899

(51) Int. Cl.
*A61B 17/04*   (2006.01)
*A61B 17/06*   (2006.01)

(52) U.S. Cl.
CPC ...... *A61B 17/0469* (2013.01); *A61B 17/0401* (2013.01); *A61B 2017/0409* (2013.01); *A61B 2017/0412* (2013.01); *A61B 2017/0432* (2013.01); *A61B 2017/06042* (2013.01); *A61B 2017/06095* (2013.01)

(58) Field of Classification Search
CPC ........ A61B 17/0401; A61B 2017/0412; A61B 2017/0432; A61B 2017/06042; A61B 2017/06095; A61B 2017/0429; A61B 2017/043; A61B 2017/0427; A61B 2017/0433
See application file for complete search history.

(56) References Cited

U.S. PATENT DOCUMENTS

| | | |
|---|---|---|
| 5,968,078 A | 10/1999 | Grotz |
| 6,626,916 B1 | 9/2003 | Yeung et al. |
| 7,780,701 B1 * | 8/2010 | Meridew et al. ............. 606/232 |
| 2006/0201519 A1 * | 9/2006 | Frazier et al. ................ 128/848 |
| 2007/0142838 A1 | 6/2007 | Jordan |
| 2010/0292732 A1 * | 11/2010 | Hirotsuka .......... A61B 17/0401 606/232 |
| 2011/0004242 A1 * | 1/2011 | Stchur ........................... 606/232 |
| 2011/0029016 A1 * | 2/2011 | Yeung ................ A61B 17/0401 606/219 |

OTHER PUBLICATIONS

International Search report dated May 8, 2012.

* cited by examiner

*Primary Examiner* — Diane Yabut
*Assistant Examiner* — Martin T Ton
(74) *Attorney, Agent, or Firm* — Bachman & LaPointe, PC

(57) ABSTRACT

In a meniscus reattachment device, with at least one needle and at least one implant, the implant is intended to have at least one extensible subsidiary surface.

8 Claims, 1 Drawing Sheet

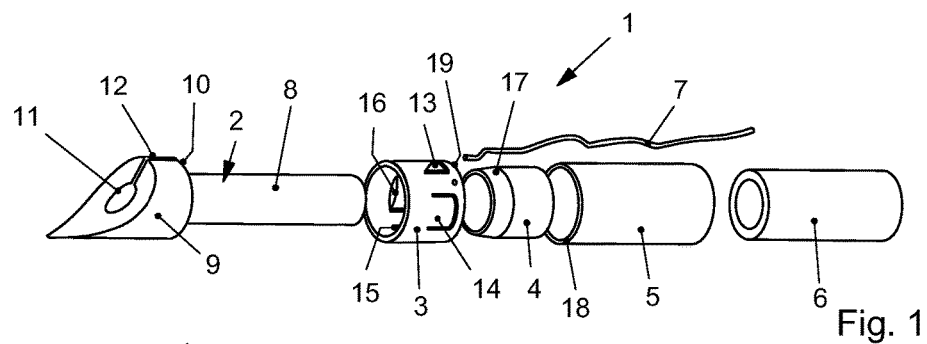
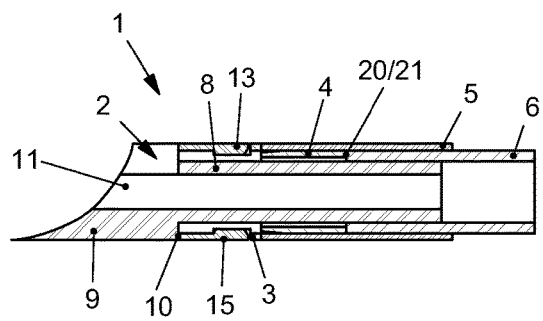
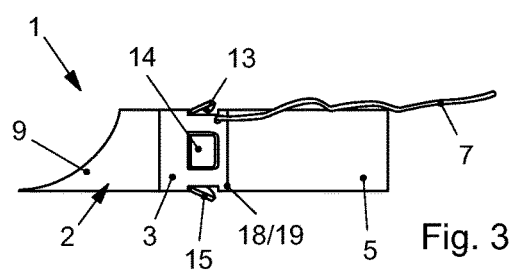 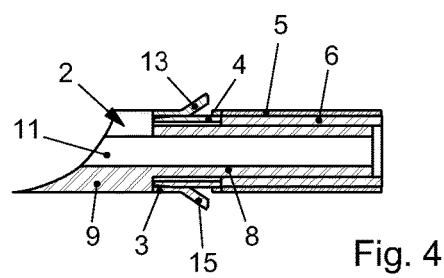
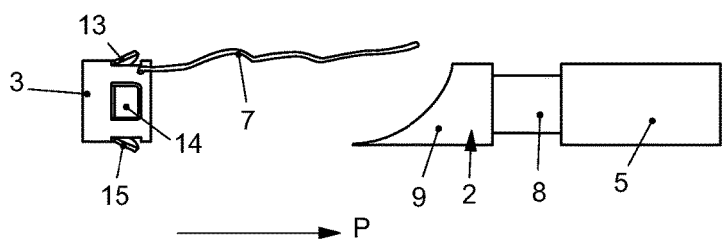
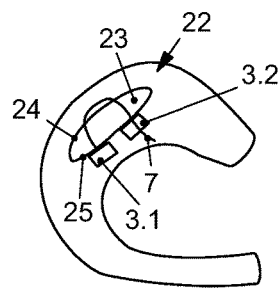 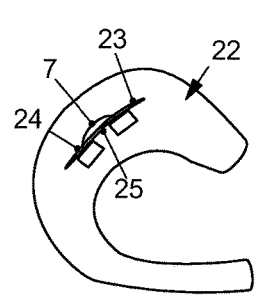

MENISCUS REATTACHMENT DEVICE

TECHNICAL FIELD

The invention relates to a Meniscus reattachment device.

PRIOR ART

The prior art discloses many devices and methods for reattachment of a meniscus. For this purpose, a plurality of anchors or suture anchors are introduced as implants into the margins of the tear, and the tear is reattached by means of a suture thread. To introduce the anchor, a needle is equipped with an anchor and a suture thread. The needle is removed rearward from the anchor in the direction of insertion, and the suture thread is knotted on the anchor. After the needles have been removed and the suture thread cut off, this knot remains behind in the tissue and causes discomfort and irritation. The knot also cuts into the cartilage tissue or even into adjoining bone tissue. Modern operating techniques and methods tolerate the cutting-in of the knots and of the thread ends into surrounding tissue, since no better methods or possible solutions are known.

SUMMARY OF THE INVENTION

The object of the invention is to make available a device that eliminates or at least minimizes the above-mentioned disadvantages.

A meniscus reattachment device preferably comprises a needle and an implant, wherein the implant has an extensible subsidiary surface. The implant is preferably designed as a tubular piece which is received on a shaft of the needle. The fact that the subsidiary surfaces, also known in the specialist literature as wings, spread open at the proximal end ensures that inadvertent removal or pulling-out of the implant becomes impossible. Here, proximal denotes a spreading-open into the cartilage tissue adjoining the meniscus.

In the specialist literature, the term anchor or suture anchor is also often used to denote the component referred to in the present application as an implant. The three terms are used in parallel in the present application.

The meniscus reattachment device preferably comprises an expansion ring, suitable for spreading open the subsidiary surface of the implant. This has the advantage that the subsidiary surfaces can be spread open only when the implant is correctly positioned. A further advantage is that the implant, with subsidiary surfaces not spread open, can be positioned in a way that is much gentler on the surrounding tissue. The expansion ring is expediently designed as a tubular piece and has an outer contour suitable for spreading open the subsidiary surfaces of the implant.

Both the implant and also the expansion ring are expediently received on a shaft of the needle. The needle preferably has a shoulder that serves as a limit stop for the implant. Using an operating device, the expansion ring can be driven into the implant in such a way that it spreads open the outwardly extensible subsidiary surfaces of the implant. It is particularly preferable for the expansion ring to have a cone-shaped or partially cone-shaped design.

In typical illustrative embodiments, the device comprises a suture thread. Preferably, the implant comprises a suture thread. Particularly preferably, the expansion ring is suitable for fixing the suture thread on the implant. This has the advantage that the device permits knot-free suturing or knot-free meniscus reattachment.

The expansion ring expediently closes the implant with the suture thread, such that the implant also has no areas that chafe against the surrounding tissue. Particularly preferably, the expansion ring also remains with the implant in the tissue.

The device expediently comprises a push rod. The push rod is preferably suitable for introducing the expansion ring into the implant. Particularly preferably, the push rod is a tubular piece which is likewise received on the shaft of the needle and adjoins a rear edge of the expansion ring. This has the advantage that the device is of very simple construction.

In typical illustrative embodiments, the needle, in particular a front part of the needle, is plastically deformable by a force. The force preferably acts on the needle, or the front part of the needle, when the expansion ring has been pressed into the implant and, by means of the push rod, moves the implant further in the direction of insertion. The resulting plastic deformation of the needle has the effect that the implant is pushed distally over the deformed needle. The outwardly extensible subsidiary surfaces hook themselves in the tissue. The needle can then be pulled out of the tissue counter to the direction of insertion.

For this purpose, the needle is expediently made of a material that is hard enough to penetrate the tissue, particularly meniscal tissue.

The device expediently comprises a tubular shaft, suitable for receiving the needle. Preferably, the implant and the expansion ring and at least part of the push rod are also received in the tubular shaft. This has the advantage that the components are protected in the tubular shaft. Furthermore, it is also advantageous that the device can be more easily introduced into the joint through the tubular shaft.

In typical illustrative embodiments, two needles, each equipped with a suture thread, an anchor and an expansion ring, are received in the tubular shaft. This has the advantage that, in the case of a lesion, two anchoring points can be applied to the meniscus.

The two needles are preferably connected via a thread bridge. This has the advantage that the tear in the meniscus can be reduced by pulling on the suture thread. For this purpose, the suture thread at the second anchor point, or at the second implant, is not yet secured between the expansion ring and the implant of the second needle, and instead can still be positioned there and drawn tight.

The components or at least some of the components of the device are expediently made of PEEK (polyether ketone) or a similar plastic, in particular plastics that have been approved for medical use. Materials are preferably used that are medical-grade materials.

In typical illustrative embodiments, the push rod is flexible in a distal area, preferably designed as a spiral wire. Particularly preferably, the flexible push rod comprises a rigid pressure plate. This has the advantage of ensuring a controlled introduction of force even along a curved needle.

Protection is claimed separately for use of a meniscus reattachment device having the described features.

BRIEF DESCRIPTION OF THE DRAWINGS

The invention is briefly described below with reference to the appended figures, in which:

FIG. 1 shows a schematic representation of a perspective exploded view of a device according to the invention;

FIG. 2 shows a schematic sectional view of the meniscus reattachment device according to the invention in the assembled state;

FIG. 3 shows a schematic representation of a side view of the meniscus reattachment device according to the invention in a further implantation step;

FIG. 4 shows a schematic sectional representation of the side view of the meniscus reattachment device according to FIG. 3;

FIG. 5 shows a schematic representation of a side view of the meniscus reattachment device in a further implantation step;

FIG. 6 shows a schematic representation of a side view of a meniscus with a tear;

FIG. 7 shows a schematic representation of a plan view of a meniscus according to FIG. 6, wherein the tear has been reattached using a device according to the invention as shown in FIGS. 1 to 5.

ILLUSTRATIVE EMBODIMENT

FIG. 1 shows a device 1 according to the invention. The device 1 comprises a needle 2, an implant 3, an expansion ring 4, a tubular shaft 5, a push rod 6, and a suture thread 7.

The needle 2 comprises a shaft 8 and a front part 9. The shaft 8 of the needle 2 has a smaller diameter than a front part 9 of the needle 2. The needle 2 thus forms a shoulder 10. Parallel to its longitudinal axis, the needle 2 has a bore 11. Moreover, in its front part 9, the needle 10 comprises a slit 12. The slit 12 extends through the front part 9 as far as the bore 11. Analogously, the shaft 8 of the needle 2 has a slit (not shown). The slit that is not shown extends from an end of the needle 2 to the front part 9 of the needle 2.

The implant 3 is a tubular piece with an internal diameter larger than an external diameter of the shaft 8 of the needle 2. Moreover, the implant 3 has four extensible subsidiary surfaces 13, 14, 15 and 16.

FIG. 2 shows the device 1 according to the invention in a state in which the device 1 is introduced into tissue, particularly a knee joint.

As is shown in FIG. 2, the implant 3 is pushed onto the shaft 8 of the needle 2. The shoulder 10 of the needle 2 serves as a limit stop for the implant 3 and ensures that the implant 3 cannot slip over the front part 9 of the needle 2.

The expansion ring 4 is likewise positioned on the shaft 8 of the needle 2. The expansion ring 4 is a tubular piece which, at a front end, has a bevel 17. An external diameter of the expansion ring 4 is smaller than an internal diameter of the implant 3. An internal diameter of the expansion ring 4 is larger than an external diameter of the shaft 8 of the needle 2.

As can likewise be seen from FIG. 2, the tubular shaft 5 is also positioned on the shaft 8 of the needle 2. A front edge 18 of the tubular shaft 5 adjoins a rear edge 19 of the implant 3. The expansion ring 4 is received in the tubular shaft 5.

Moreover, the pusher 6 is received at least partially on the shaft 8 of the needle 2. The pusher 6 is likewise a tubular piece, with an external diameter smaller than an internal diameter of the tubular shaft 5. The pusher 6 is likewise received at least partially in the tubular shaft 5. With a front edge 20, the pusher 6 bears on a rear edge 21 of the expansion ring 4.

The function of the present invention is as follows:

FIG. 6 shows a schematic side view of a meniscus 22 with a tear 23.

For better clarity, a first implant in FIGS. 6 and 7 is designated by reference sign 3.1 and a second implant by reference sign 3.2. These implants are preferably identical and correspond to the structure of the described implant 3.

For meniscus reattachment, two needles, each equipped with a respective implant 3.1, 3.2 and with a suture thread 7 and expansion ring, and connected via a common operating device (not shown), are introduced into the joint in a manner parallel to the tear 23.

In addition to the common operating device, the two needles are also connected by a thread bridge (not shown).

The two needles are preferably placed in a common sheath. The common sheath serves to protect the needles and. the component parts and. to permit easier insertion of the device into the joint.

In preferred illustrative embodiments, the tubular shaft is designed such that it can receive two needles, which are each equipped with an implant, a suture thread, an expansion ring and possibly also with a pusher.

For the further description. of the use of the device 1 according to the invention, it is immaterial whether the needles are received together in one sheath or are each received in a. separate sheath.

The first needle 2, equipped with the first implant 3.1, is pushed forward out of the tubular shaft 5 and, as can be seen from the course of the suture thread in FIG. 6, is introduced into the meniscus parallel to the tear 23. In the following, the introduction of an implant 3 is generally described as representative of the implantation of the implant 3.1.

By actuation of the pusher 6, the expansion ring 4, as can be seen in FIGS. 3 and 4, is pushed under the implant 3 in such a way that the subsidiary faces 13, 14, 15 and 16 spread open. This has the advantage that the implant 3 is anchored in the cartilage or meniscal tissue. By means of the expansion ring 4 being driven into the implant 3, the suture thread 7 is at the same time fixed firmly in the implant 3. The tact that the subsidiary surfaces 13, 14, 15 and 16 spread open at the proximal end ensures that pulling-out of the implant becomes impossible. The suture thread 7 is advantageously fixed without a knot that could later rub on cartilage tissue or on the bone.

In medical literature, instead of the term implant, the term anchor or suture anchor is often used for a component corresponding to the implant 3 of the present invention.

The needle 2 is subsequently removed from the implant 3. For this purpose, as is shown in FIG. 5, the needle 2 is pulled rearward. in arrow direction P out of the implant 3 and out of the expansion ring 4 (not shown in FIG. 5). In doing this, the implant 3 serves as an abutment for the front part 9 of the needle 2. By means of the slit 12 and the bore 11, the front part 9 of the needle 2 is also designed such that it is plastically deformed when a certain force is reached, and it collapses in on itself in such a way that it can be removed through the implant 3 in arrow direction P.

In preferred illustrative embodiments, at least the front part 9 of the needle 2 is made from a material which is sufficiently hard and strong enough to penetrate tissue, particularly cartilage tissue. However, the material of the front part 9 orate needle 2 is softer than a material of the implant 3, such that the implant 3 can serve as abutment.

After the first needle 2 has been removed, the implant 3, with the suture thread 7 and. the expansion ring 4, remains in the meniscus 22.

With the second needle, which is connected to the already inserted implant 3.1 via the suture thread 7 or the thread bridge, the second implant 3.2 is positioned analogously with respect to the tear 23.

As is shown. in FIGS. 6 and 7, the suture thread 7 is secured with the implants 3.1 and 3.2 as a loop across the tear 23. The insertion of the second implant 3.2 takes place analogously to the fixing of the first implant 3.1. Before the expansion ring 4 is driven into the second implant 3.2 in order to fix the suture thread 7 and spread open the subsidiary surfaces 13, 14, 15 and 16, the tear 23 is closed by pulling on the suture thread 7, as is shown in FIG. 7. Finally, the second needle is removed from the implant 3.2 and the suture thread 7 is cut off.

The invention claimed is:

1. A meniscus reattachment device (1), comprising at least one needle (2), comprising a shaft (8), and a front part (9), at least one implant (3), wherein the implant (3) has at least one extensible subsidiary surface (13, 14, 15, 16), a suture thread (7), and
a tubular expansion ring (4) having an external diameter smaller than an internal diameter of the implant (3), an internal diameter larger than an external diameter of the shaft (8), and a bevel (17) facing the front part (9) of the needle (2), the expansion ring (4) being sized relative to the at least one extensible subsidiary surface (13, 14, 15, 16) for spreading open the at least one subsidiary surface (13, 14, 15, 16) of the implant (3) and fixing the suture thread (7) on the implant (3) when the expansion ring (4) is pressed into the implant (3).
wherein the shaft (8) is smaller in diameter than the front part (9), and
wherein the needle (2) has a longitudinal axis and a bore (11) parallel to the longitudinal axis, and a slit (12) extending through the front part (9) to the bore (11).

2. The device according to claim 1, further comprising a push rod (6), suitable for introducing the expansion ring (4) into the implant (3).

3. The device according to claim 1, wherein the needle (2) is plastically deformable by a force.

4. The device according to claim 1, further comprising a tubular shaft (5), suitable for receiving the needle (2).

5. The device according to claim 1, further comprising a flexible push rod, by means of which a force can be introduced along a curved needle by means of a pressure plate.

6. The device according to claim 1, wherein the at least one implant (3) and the expansion ring (4) fit over the shaft (8) in advance of insertion of the implant (3) to a meniscus.

7. A method of inserting at least one implant (3) for reattaching a meniscus (23), comprising the steps of:
pressing a meniscus reattachment device (1), by a push rod (6), into a meniscus, the meniscus reattachment device (1) comprising:
at least one plastically deformable needle (2) comprising a shaft (8) and a front part (9), wherein the shaft (8) is smaller in diameter than the front part (9),
an implant (3) which has at least one extensible subsidiary surface (13, 14, 15, 16),
a suture thread (7),
a tubular expansion ring (4) having an external diameter smaller than an internal diameter of the implant (3), an internal diameter larger than an external diameter of the shaft (8), and a bevel (17) facing the front part of the needle (9) suitable for spreading open the at least one subsidiary surface (13, 14, 15, 16) of the implant (3) and fixing the suture thread (7) on the implant (3), wherein the needle (2) has a longitudinal axis and a bore (11) parallel to the longitudinal axis, and a slit (12) extending through the front part (9) to the bore (11);
pressing the expansion ring (4) into the implant (3), whereby the expansion ring (4) forces the at least one extensible subsidiary surface (13, 14, 15, 16) to expand and hold the implant relative to the meniscus; and
pulling the needle(2) proximally relative to the implant(3) whereby the needle (2) deforms and implant (3) moves distally over the needle (2) such that the needle (2) separates from the implant (3).

8. A meniscus reattachment device (1), comprising
at least one plastically deformable needle (2), comprising a shaft (8), and a front part (9),
a tubular implant (3), fitting over the shaft, having at least one extensible subsidiary surface (13, 14, 15, 16),
a suture thread (7) passing through the tubular implant,
a tubular expansion ring (4) having an external diameter smaller than an internal diameter of the implant (3), an internal diameter larger than an external diameter of the shaft (8), and a bevel (17) facing the front part (9) of the needle (2), the expansion ring (4) being sized relative to the at least one extensible subsidiary surface (13, 14, 15, 16) for spreading open the at least one subsidiary surface (13, 14, 15, 16) of the implant (3) and fixing the suture thread (7) on the implant (3) when the expansion ring (4) is pressed into the implant (3),
wherein the needle (2) is deformable such that when the implant (3) is pushed toward the needle (2) in a direction of insertion, the needle (2) deforms and can be pulled out of the implant (3) counter to the direction of insertion and thereby separated from the implant (3), and
wherein the shaft (8) is smaller in diameter than the front part (9), and
wherein the needle (2) has a longitudinal axis and a bore (6) parallel to the longitudinal axis, and a slit (12) extending through the front part (9) to the bore (11).

* * * * *